US009625390B2

(12) United States Patent
Antunovich et al.

(10) Patent No.: US 9,625,390 B2
(45) Date of Patent: *Apr. 18, 2017

(54) DETERMINING PERCENT SOLIDS IN SUSPENSION USING RAMAN SPECTROSCOPY

(71) Applicant: MannKind Corporation, Valencia, CA (US)

(72) Inventors: Jason J. Antunovich, Danbury, CT (US); Arthur T. Hamfeldt, Poughquag, NY (US); Rodney J. Woods, New Milford, CT (US); Sam C. Shum, New Milford, CT (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/194,630

(22) Filed: Jun. 28, 2016

(65) Prior Publication Data

US 2016/0305886 A1 Oct. 20, 2016

Related U.S. Application Data

(63) Continuation of application No. 14/840,116, filed on Aug. 31, 2015, now Pat. No. 9,389,185, which is a
(Continued)

(51) Int. Cl.
*G01J 3/44* (2006.01)
*G01N 21/65* (2006.01)
(Continued)

(52) U.S. Cl.
CPC .............. *G01N 21/65* (2013.01); *G01G 9/00* (2013.01); *G01N 15/06* (2013.01);
(Continued)

(58) Field of Classification Search
CPC ... G01J 3/44; G01J 3/02; G01N 21/65; G01N 21/658; G01N 2021/656
See application file for complete search history.

(56) References Cited

U.S. PATENT DOCUMENTS 4,172,884 A   10/1979   Christe et al.
4,282,745 A   8/1981   Burr
(Continued)

FOREIGN PATENT DOCUMENTS

WO   WO 2006/023943 A1   3/2006

OTHER PUBLICATIONS

Katchalski et al., "Synthesis of Lysine Anhydride", J. Amer. Chem. Soc., 68:879-80, 1946.
(Continued)

*Primary Examiner* — Abdullahi Nur
(74) *Attorney, Agent, or Firm* — Wolf, Greenfield & Sacks, P.C.

(57) ABSTRACT

Methods and apparatus are provided for determining weight percent of solids in a suspension using Raman spectroscopy. The methods can be utilized to acquire Raman spectral data from the suspension and to determine weight percent of solids in a process being carried out, for example, in a vessel, without the need to remove samples for analysis. The weight percent of the solids can be determined with a desired accuracy in a relatively short time, typically 10 minutes or less. The acquired Raman spectral data may be processed by chemometric software using, for example, a partial least squares algorithm and data pretreatment to provide a predicted value of weight percent solids. In some embodiments, the invention is used to determine the weight percent of microparticles of a diketopiperazine in an aqueous solution.

20 Claims, 6 Drawing Sheets

Related U.S. Application Data continuation of application No. 13/696,650, filed as application No. PCT/US2011/035112 on May 4, 2011, now Pat. No. 9,140,651.

(60) Provisional application No. 61/332,292, filed on May 7, 2010.

(51) Int. Cl.
  *G01G 9/00* (2006.01)
  *G01N 15/06* (2006.01)

(52) U.S. Cl.
  CPC .............. *G01N 2201/06113* (2013.01); *G01N 2201/121* (2013.01); *G01N 2201/127* (2013.01)

(56) References Cited

U.S. PATENT DOCUMENTS

| | | | |
|---|---|---|---|
| 5,352,461 A | 10/1994 | Feldstein et al. | |
| 5,503,852 A | 4/1996 | Steiner et al. | |
| 5,596,196 A | 1/1997 | Cooper et al. | |
| 5,786,893 A | 7/1998 | Fink et al. | |
| 6,071,497 A | 6/2000 | Steiner et al. | |
| 6,331,318 B1 | 12/2001 | Milstein | |
| 6,428,771 B1 | 8/2002 | Steiner et al. | |
| 6,440,463 B1 | 8/2002 | Feldstein et al. | |
| 6,444,226 B1 | 9/2002 | Steiner et al. | |
| 6,652,885 B2 | 11/2003 | Steiner et al. | |
| 7,709,639 B2 | 5/2010 | Stevenson et al. | |
| 7,799,344 B2 | 9/2010 | Oberg | |
| 7,803,404 B2 | 9/2010 | Hokenson et al. | |
| 7,820,676 B2 | 10/2010 | Leone-Bay et al. | |
| 8,039,431 B2 | 10/2011 | Wilson et al. | |
| 9,140,651 B2 * | 9/2015 | Antunovich | G01N 21/65 |
| 9,389,185 B2 * | 7/2016 | Antunovich | G01N 21/65 |
| 2002/0156380 A1 | 10/2002 | Feld et al. | |
| 2003/0083355 A1 | 5/2003 | Bonifacio et al. | |
| 2003/0119199 A1 | 6/2003 | Wolf et al. | |
| 2005/0183836 A1 | 8/2005 | Satyavolu et al. | |
| 2006/0099269 A1 | 5/2006 | Cheatham et al. | |
| 2007/0196503 A1 | 8/2007 | Wilson et al. | |
| 2008/0166958 A1 | 7/2008 | Golden et al. | |
| 2008/0177481 A1 | 7/2008 | Popp et al. | |
| 2008/0268548 A1 | 10/2008 | Zuckerman | |
| 2008/0306346 A1 | 12/2008 | Claus et al. | |
| 2012/0145907 A1 | 6/2012 | Van Groos | |
| 2012/0164186 A1 | 6/2012 | Grant et al. | |
| 2015/0369743 A1 | 12/2015 | Antunovich et al. | |

OTHER PUBLICATIONS

Kopple et al., "A Convenient Synthesis of 2,5-Piperazinediones", J. Org. Chem., 33:862-64, 1968.

* cited by examiner

| Wavelength Resampling Interval | 0.04 nm | Result Spectrum | Counts |
|---|---|---|---|
| Wavenumber resampling interval | 0.3 cm$^{-1}$ | Dark Spectrum Acquisition | 1/day |
| Fourier Interpolation | 4x | Wavelength Region | 0.00 cm$^{-1}$–3450.00 cm$^{-1}$ |
| Fourier weighting | Hanning–cosine squared | Laser wavelength | 785 nm |
| Resampling Method | Cubic spline | Detector | CCD (Andor) |
| Exposure Time | 45 s | | |
| Accumulations | 4 | | |
| Cosmic Ray Filtration | Yes | | |

FIG. 4

| | |
|---|---|
| Software | Unscrambler ver9.8 |
| Model Name | PLS1 1PC 1D CMD 2&3 PQ 1&3 |
| Data Pre-treatment | S-G 1st Deriv., 3 pts., 2nd order polynomial |
| Model Type | PLS1 |
| | Full |
| | Data Centered |
| Validation Method | Leverage Correction |
| Wavenumber Region | 1180 – 1800 cm$^{-1}$, 2782 – 3136 cm$^{-1}$ |
| PC | 2 |
| Residual Y-validation Variance | 0.009 |
| R$^2$ | 0.999 |
| RMSE | 0.084 |

FIG. 5

DETERMINING PERCENT SOLIDS IN SUSPENSION USING RAMAN SPECTROSCOPY

CROSS REFERENCE TO RELATED APPLICATIONS

This application is a continuation of U.S. patent application Ser. No. 14/840,116, filed Aug. 31, 2015, which is a continuation of U.S. patent application Ser. No. 13/696,650, filed Nov. 7, 2012, which is a national stage of PCT/US2011/035112, filed May 4, 2011, which claims priority based on Provisional Application Ser. No. 61/332,292, filed May 7, 2010, which are hereby incorporated by reference in their entirety.

FIELD OF THE INVENTION

This invention relates to methods and apparatus for measuring percent solids of particles in a suspension using Raman spectroscopy. The invention can be used to provide real time results in a commercial manufacturing environment, but is not limited to such use.

BACKGROUND OF THE INVENTION

A variety of processes for making products, including products in the food and pharmaceutical industries, utilize steps with particles in suspension for use in a variety of applications. In one example, it has been proposed to deliver certain types of drugs to patients by inhalation of powder particles as a delivery mechanism. One particular example uses microparticles comprising diketopiperazine, known as Technosphere® microparticles. The Technosphere microparticles have a platelet surface structure and can be loaded with a drug. One use of these microparticles is for the delivery of insulin by inhalation.

An exemplary process for making Technosphere microparticles begins with raw materials, including acetic acid and fumaryl diketopiperazine (FDKP) to precipitate the Technosphere particles out of solution to form a suspension. Using a tangential flow filter, the particles are washed using diafiltration, and the concentration of the particles is increased by removing liquid. Insulin is added to the suspension to form a Technosphere Insulin (TI) suspension. The suspension is flash frozen to make pellets that are dried in a bulk lyophilization process to remove the liquid components. Dry TI powder removed from the lyophilizer is packed into containers for later filling of inhaler cartridges.

During manufacturing of Technosphere Insulin, a process tank receives the suspension of Technosphere particles after the tangential flow filtration and concentration steps at approximately 10% solids by weight. The suspension is stirred continuously prior to and during insulin addition. Insulin solution preparation does not proceed until an actual percent solids value of the suspension is determined.

Existing methods for determining percent solids of Technosphere particles in the suspension are slow and are subject to errors. One existing method involves taking one or more samples of the Technosphere suspension, drying the suspension in a microwave oven and weighing the remaining solids. The process typically requires two to three hours and is subject to measurement errors.

Accordingly, there is a need for improved methods and apparatus for determining percent solids in a suspension.

SUMMARY OF THE INVENTION

Embodiments of the invention provide methods and apparatus for determining weight percent of solids in a suspension using Raman spectroscopy. The methods can be utilized to acquire Raman spectral data from the suspension and to determine weight percent of solids in a process being carried out, for example, in a vessel, without the need to remove samples for analysis. The weight percent of the solids can be determined with a desired accuracy in a relatively short time, typically 10 minutes or less. The acquired Raman spectral data may be processed, for example, by chemometric software using a partial least squares algorithm and data pretreatment, to provide a predicted value of weight percent solids. In some embodiments, the invention is used to determine the weight percent of microparticles of a diketopiperazine in an aqueous solution. The invention is particularly useful for determining weight percent of solids in a range of 5% to 20%, but is not limited to this range.

According to a first embodiment, a method is provided for determining weight percent of solids in a suspension. The method comprises mixing the suspension, acquiring Raman spectral data of the solids in the suspension, and processing the Raman spectral data to determine weight percent of the solids in the suspension.

According to a second embodiment, an apparatus is provided for determining weight percent of solids in a suspension. The apparatus comprises a Raman spectrometer to acquire Raman spectral data of the solids in the suspension, and a computing device including a processor and a computer-readable storage medium, the computer-readable storage medium containing computer instructions that, when executed by the processor, perform a method of processing the Raman spectral data to determine weight percent of the solids in the suspension.

According to a third embodiment, a method is provided for determining weight percent of solids. The method comprises mixing a suspension to distribute the solids; acquiring spectral data from the suspension utilizing a probe and a Raman spectrometer; processing the spectral data; and determining weight percent of the solids in the suspension. In this embodiment, the probe utilized to acquire the Raman spectral data can be used in situ, wherein the probe can be immersed in the suspension. In one embodiment, the probe can be an optical device or an optical sensor, such as a short focus optical device. In another embodiment, the probe can be used without being immersed in the suspension, for example, the probe can comprise, for example, a beam that can penetrate the suspension; the beam can generate a Raman spectrum from the particles. The Raman spectrum generated by the particles can be acquired by the spectrophotometer. In yet another embodiment, Raman spectral data can be acquired with another type of optical sensor.

BRIEF DESCRIPTION OF THE DRAWINGS

For a better understanding of the present invention, reference is made to the accompanying drawings, which are incorporated herein by reference and in which:

FIG. 4 is a tabulation of Raman spectrometer parameters used to determine weight percent of solids in a suspension, in accordance with embodiments of the invention;

FIG. 5 is a tabulation of model parameters and results for determining weight percent of solids in a suspension, in accordance with embodiments of the invention;

DETAILED DESCRIPTION

Embodiments of the invention provide methods and apparatus for determining weight percent of solids in a suspension using Raman spectroscopy. The methods can be utilized to determine weight percent of solids in a suspension without the need to remove samples for analysis. The weight percent of solids can be determined with a desired accuracy in a relatively short time, typically ten minutes or less.

Figure 1:
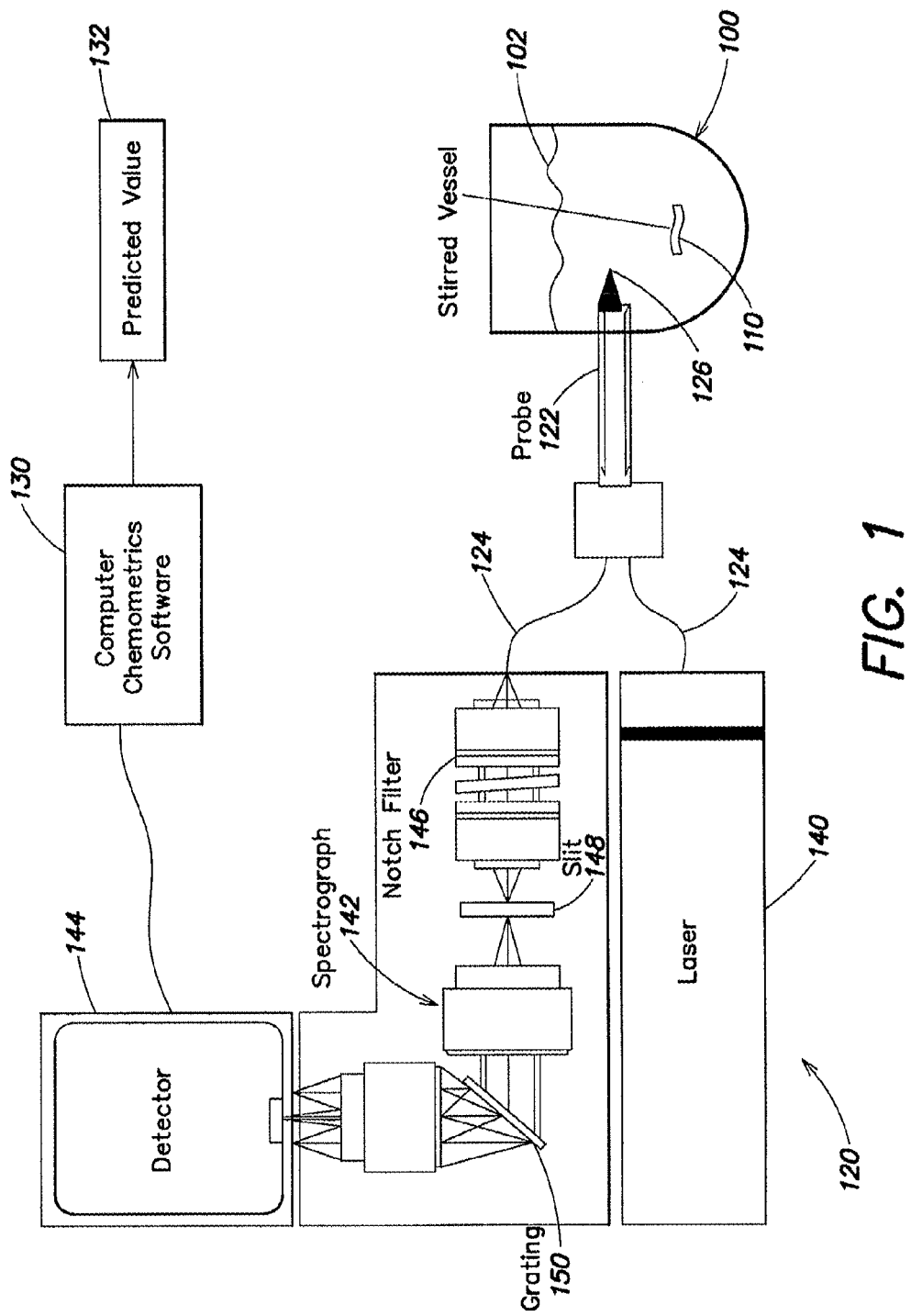
FIG. 1 is a schematic block diagram of a system for determining weight percent of solids in a suspension, in accordance with embodiments of the invention.

The components of a system for determining weight percent of solids in a suspension, in accordance with embodiments of the invention, are shown in FIG. 1. A vessel 100 contains a suspension 102 of solid particles for which the weight percent of solids is to be measured. A mixing device 110 ensures that the suspension 102 is mixed, at least during acquisition of Raman spectral data. The vessel 100 may be any suitable size and may be a component of a production process.

While FIG. 1 shows vessel 100, the suspension can be in any type of container, such as a vessel, flask, beaker or pipe, during acquisition of Raman spectral data. The container can have any size and shape. In some embodiments, the suspension is in a process vessel or pipe, and Raman spectral data is acquired before, during and/or after a process. In other embodiments, the suspension is in a test container, such as a beaker or flask, and Raman spectral data is acquired off-line or in a laboratory environment. Mixing the suspension may entail various mechanisms. In the process, the suspension may be mixed, stirred, caused to flow, or otherwise agitated in the container. This ensures that the distribution of particles in the region of Raman spectral data acquisition is more or less uniform and is representative of the process being analyzed.

In one specific example, suspension 102 is an aqueous suspension of particles comprising a compound represented by the formula 1 such as a diketopiperazine. As used herein, "diketopiperazine" or "DKP" includes diketopiperazines and salts, derivatives, analogs and modifications thereof falling within the scope of the general Formula 1, wherein the ring atoms E1 and E2 at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

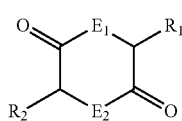

Formula 1

Diketopiperazines can be formed by cyclodimerization of amino acid ester derivatives, as described by Katchalski et al. (*J. Amer. Chem. Soc.* 68:879-80; 1946), by cyclization of dipeptide ester derivatives, or by thermal dehydration of amino acid derivatives in high-boiling solvents, as described by Kopple, et al., (*J. Org. Chem.* 33:862-64; 1968), the teachings of which are incorporated herein.

Methods for synthesis and preparation of diketopiperazines are well known to one of ordinary skill in the art and are disclosed in U.S. Pat. Nos. 5,352,461; 5,503,852; 6,071,497; 6,331,318; 6,428,771 and U.S. Patent Publication No. 2006/0040953. U.S. Pat. Nos. 6,444,226 and 6,652,885, describe preparing and providing microparticles of diketopiperazines in aqueous suspension to which a solution of active agent is added in order to bind the active agent to the particle. These patents further describe a method of removing a liquid medium by lyophilization to yield microparticles comprising an active agent. Altering the solvent conditions of such suspension to promote binding of the active agent to the particle is taught in U.S. patent application Ser. Nos. 60/717,524 and 11/532,063 both entitled "Method of Drug Formulation Based on Increasing the Affinity of Active Agents for Crystalline Microparticle Surfaces"; and Ser. No. 11/532,065 entitled "Method of Drug Formulation Based on Increasing the Affinity of Active Agents for Crystalline Microparticle Surfaces". See also U.S. Pat. No. 6,440,463 and U.S. patent application Ser. No. 11/210,709 filed on Aug. 23, 2005 and U.S. patent application Ser. No. 11/208,087. In some instances, it is contemplated that the loaded diketopiperazine particles of the present invention are dried by a method of spray drying as disclosed in, for example, U.S. patent application Ser. No. 11/678,046 filed on Feb. 22, 2006 and entitled "A Method For Improving the Pharmaceutic Properties of Microparticles Comprising Diketopiperazine and an Active Agent." Each of these patents and patent applications is incorporated by reference herein for all they contain regarding diketopiperazines.

Diketopiperazines, in addition to making aerodynamically suitable microparticles, can also facilitate the delivery of active agents by rapidly dissolving at physiologic pH thereby releasing the active agent and speeding its absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In one embodiment, the diketopiperazine is 3,6-bis[4-(N-carboxy-2-propenyl)amidobutyl]-2,5-diketopiperazine or 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di(4-aminobutyl)-2,5-diketopiperazine, which can be formed by (thermal) condensation of the amino acid lysine. Exemplary derivatives include 3,6-di(succinyl-4-aminobutyl)-2,5-diketopiperazine, 3,6-di(maleyl-4-aminobutyl)-2,5-diketopiperazine, 3,6-di(glutaryl-4-aminobutyl)-2,5-diketopiperazine, 3,6-di(malonyl-4-aminobutyl)-2,5-diketopiperazine, 3,6-di(oxalyl-4-amino-butyl)-2,5-diketopiperazine, 3,6-di(fumaryl-4-aminobutyl)-2,5-diketopiperazine or 3,6-di(citraconyl-4-aminobutyl)-2,5- diketopiperazine and derivatives therefrom. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in co-pending U.S. patent application Ser. No. 11/210,710 filed Aug. 23, 2005, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety. Further details related to adsorption of active agents onto crystalline DKP particles can be found in co-pending U.S. patent application Ser. Nos. 11/532,063 and 11/532,065, which are hereby incorporated by reference in their entirety.

In one embodiment, the microparticles in suspension can have a diameter or size greater than 0.05 micrometers. In a specific embodiment wherein the microparticles comprise a diketopiperazine, the microparticles of diketopiperazine, for example, can comprise FDKP having a size that can be in a range of 0.1 to 34 micrometers, but the particle size is not limited to this size range. The weight percent of the solid particles in the suspension is typically in a range of about 5% to 20%, but the invention is not limited to this range.

The system for determining the weight percent of solids in the suspension 102 includes a Raman spectrometer 120, a probe 122 associated with Raman spectrometer 120 and a computer 130 executing chemometric software for processing Raman spectral data acquired by Raman spectrometer 120 and providing a predicted value 132 of the weight percent of solids in suspension 102. Probe 122 may be connected to Raman spectrometer 120 by an optical fiber cable 124. Probe tip 126 of probe 122 may be inserted into suspension 102 in vessel 100. Probe tip 126 may, for example, be sealed in an opening in the wall of vessel 100.

Raman spectrometer 120 includes a laser 140 having an output that is transmitted via optical fiber cables 124 through probe 122 to vessel 100 for excitation of the particles in suspension 102. The Raman radiation stimulated by laser 140 is transmitted through probe 122 via optical fiber cables 124 and optical elements 142 to a detector 144. The optical elements may include a notch filter 146, a slit 148 and a grating 150 to select a particular wavelength range (Raman shift) for detection. The detector 144 determines the received intensity over the selected wavelength range to provide a Raman spectrum. In one embodiment, the Raman spectrometer 120 may be a model RXN-3 commercially available from Kaiser Optical Systems Inc., and the probe 122 may be a 0.5 inch short focus immersion optic, also available from Kaiser Optical Systems Inc.

The computer 130 can be a personal computer with a Windows XP operating system. In another embodiment, a microprocessor capable of acquiring Raman spectral data and processing the data obtained can be used. The computer 130 may include a non-transitory computer-readable storage medium for storage of Raman software, chemometric software, or both. Computer-readable storage media includes volatile and nonvolatile, removable and non-removable media implemented in any method or technology for storage of information such as computer-readable instructions, data structures, program modules or other data. Computer-readable storage media includes RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a processor of computer 130.

The Raman software associated with data acquisition can be Holograms software, version 4.1. The chemometric software for processing the Raman spectral data and providing a predicted value of the weight percent of solids in suspension can be Unscrambler software, version 9.8. It will be understood that other software packages or custom developed software may be utilized within the scope of the invention. Examples of parameters used for Raman spectral data acquisition and for a chemometric model for the example of an aqueous suspension of particles comprising FDKP are described below.

Figure 2:
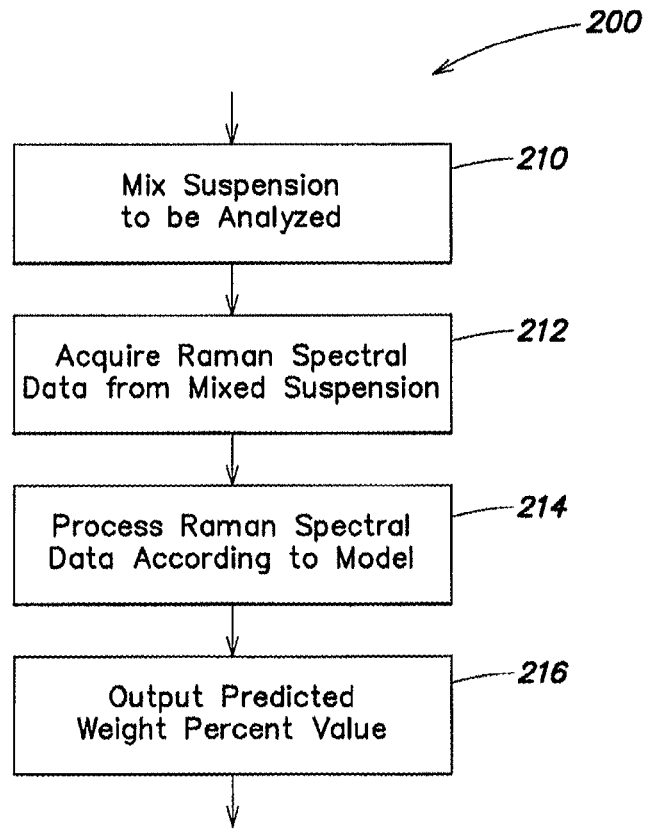
FIG. 2 is a flow diagram of a process for determining weight percent of solids in a suspension, in accordance with embodiments of the invention.

A flow diagram of a process 200 for determining weight percent of solids in a suspension, according to embodiments of the invention, is shown in FIG. 2. In act 210, the suspension to be analyzed is mixed, typically by stirring. The mixing produces a relatively uniform distribution of particles in the suspension. The mixing may continue at least until acquisition of Raman spectral data has been completed, though this may not be necessary, for example, as with slowly (with respect to the time required to acquire sufficient data for analysis) settling particles. In an industrial setting, the mixing process can be continuous.

In act 212, the Raman spectrometer 120 and probe 122 are used to acquire Raman spectral data from the mixed suspension 102 in vessel 100. As discussed below, the Raman spectral data is acquired over one or more spectral ranges. The detector 144 of Raman spectrometer 120 detects the Raman shift produced by suspension 102 in response to the energy from laser 140 and records the spectral data in a memory in computer 130. Raman parameters for acquisition of Raman spectral data from Technosphere particles are discussed below.

In act 214, the chemometric software in computer 130 processes the acquired Raman spectral data according to a chemometric model. The chemometric model provides calibration information to be used by the chemometric software in processing the Raman spectral data. The calibration information may include reference data which is obtained by a gravimetric measurement method. The chemometric model is selected to provide a highly accurate prediction of the weight percent of solids in suspension 102 over a range of expected conditions. The chemometric model is discussed below. In act 216, the chemometric software outputs a predicted weight percent value based on the acquired Raman spectral data.

Figure 3:
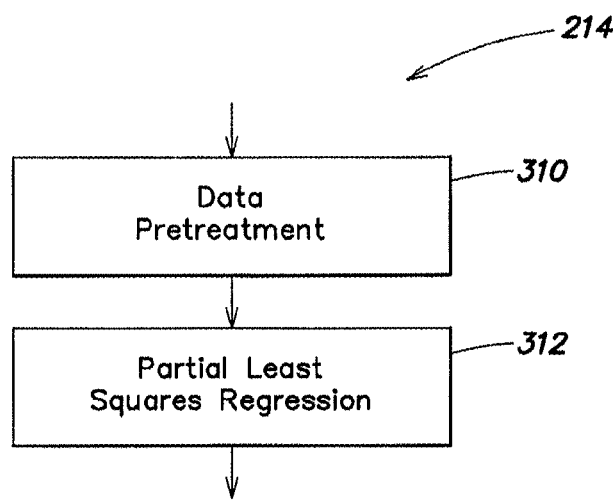
FIG. 3 is a flow diagram that illustrates processing of the Raman spectral data to determine weight percent of solids in a suspension, in accordance with embodiments of the invention.

An embodiment of the processing of act 214 is shown in FIG. 3. Data pretreatment of the Raman spectral data may be performed in act 310 to remove or minimize spectral variations. The result of data pretreatment may be processed by partial least squares regression in act 312 using a model as described below.

By way of example only, embodiments of the invention may be used to determine weight percent of solids in an aqueous suspension of particles comprising FDKP. In a typical application, the particles comprising FDKP are in a size range of 0.1 to 34 micrometers, and the weight percent of solids is in a range of 10% to 12%. More generally, embodiments of the invention may be used to determine weight percent of solids in suspensions in a range of 5% to 20%, but the invention is not limited to this range. It will be understood that different Raman spectrometer parameters and model parameters may be used for analyzing different particle types, different particle sizes and/or different weight percent ranges.

Examples of parameters used by the Raman spectrometer 120 and its operating software for acquisition of Raman spectral data from an aqueous suspension of particles comprising FDKP are summarized in FIG. 4. As shown in FIG. 4, the laser wavelength may be 785 nanometers, and the Raman shift region may be 0.00 $cm^{-1}$ to 3450.00 $cm^{-1}$. The wavenumber re-sampling interval may be 0.3 $cm^{-1}$. In one embodiment, for detection of particles comprising FDKP, the wavenumber regions of interest may be 1180-1800 $cm^{-1}$ and 2782-3136 $cm^{-1}$ as shown in FIG. 5. It will be understood that different wavenumber regions of interest may be used for sampling of different particle types, based on the chemistry and physical properties of the particles.

In the example of FIG. 4, the exposure time may be 45 seconds, the number of accumulations may be four, and cosmic ray filtration may be utilized. The exposure time is the interval during which the detector 144 is made available to receive the Raman signal. The accumulation number is the quantity of discrete exposure intervals. Cosmic ray filtration is a software process that removes erratic signals that may arise during sample analysis due to energetic cosmic ray particles interacting with the detector. The total time of analysis for a sample is the accumulation number multiplied by the exposure time multiplied by two (for cosmic ray filtration). Thus, in the example of FIG. 4, the total time for analysis of a sample is 6 minutes. The analysis time is typically less than 10 minutes. The parameters can be selected such that an optimal balance is achieved between the total time of analysis with requirements for real-time in-situ measurement and sufficient signal to noise.

The chemometric model utilized by computer 130 in processing the Raman spectral data in this example is summarized in FIG. 5. As shown, the chemometric model is based on Unscrambler software, version 9.8, a commercially available chemometric software package. In this embodiment, the chemometric model employs a partial least squares algorithm with data pretreatment. In some embodiments, the Raman spectral data is processed by executing a regression algorithm including partial least squares, multiple linear regression, or principal component regression, with or without data pretreatment.

The data pretreatment utilized may be Savitzky-Golay first derivative data pretreatment. It will be understood that different data pretreatment techniques can be utilized. Other data pretreatment techniques may include, but are not limited to, multiplicative and extended multiplicative scatter correction, standard normal variate, various derivatives and normalizations. In some embodiments, no pretreatment of the data is required.

The model data is centered, the model size is full, the validation method is leverage correction and maximum principal components (PCs) is set to a value of 9. Typically, more PCs than would be expected are chosen. Model size indicates the number of result matrices available for display after calibration, i.e. residuals, variance plot, etc. Leverage correction validation method provides an estimate of prediction quality, i.e., root mean square error (RMSE) values. The parameter $R^2$ is a correlation coefficient output by the regression calculation.

In one embodiment, the number of PCs selected minimizes variance without overfitting. The user can verify the validity of the number of PCs selected by inspecting the residual validation variance curve. The number of PCs is selected at or just above the characteristic elbow seen in the plot of Y variance versus PC number. The residual variance observed utilizing two PCs in this example is 0.009 units. The degree to which the model is overfitting the data can be evaluated by the performance of the model in predicting new samples.

Mathematical pretreatment, or preprocessing of various types can be utilized to remove or minimize undesired spectral variations. Spectral variations may occur as a result of variation in many different physical properties, including but not limited to particle size, refractive index, temperature, etc.

The chemometric model was developed by acquiring Raman spectra of particles comprising FDKP in suspensions at concentrations ranging from approximately 7.00 to 16.00 weight percent. The process samples were concentrated and diluted appropriately. Reference percent solids data (Y-data) was measured for each sample by microwave oven loss on drying methodology (reference gravimetric methodology), where % S=100*(dry weight/wet weight). Raman spectral data (X-data) are imported into the Unscrambler software, version 9.8 with the reference % S values (Y-data). Partial least squares (PLS) processing is then performed.

Figure 6:
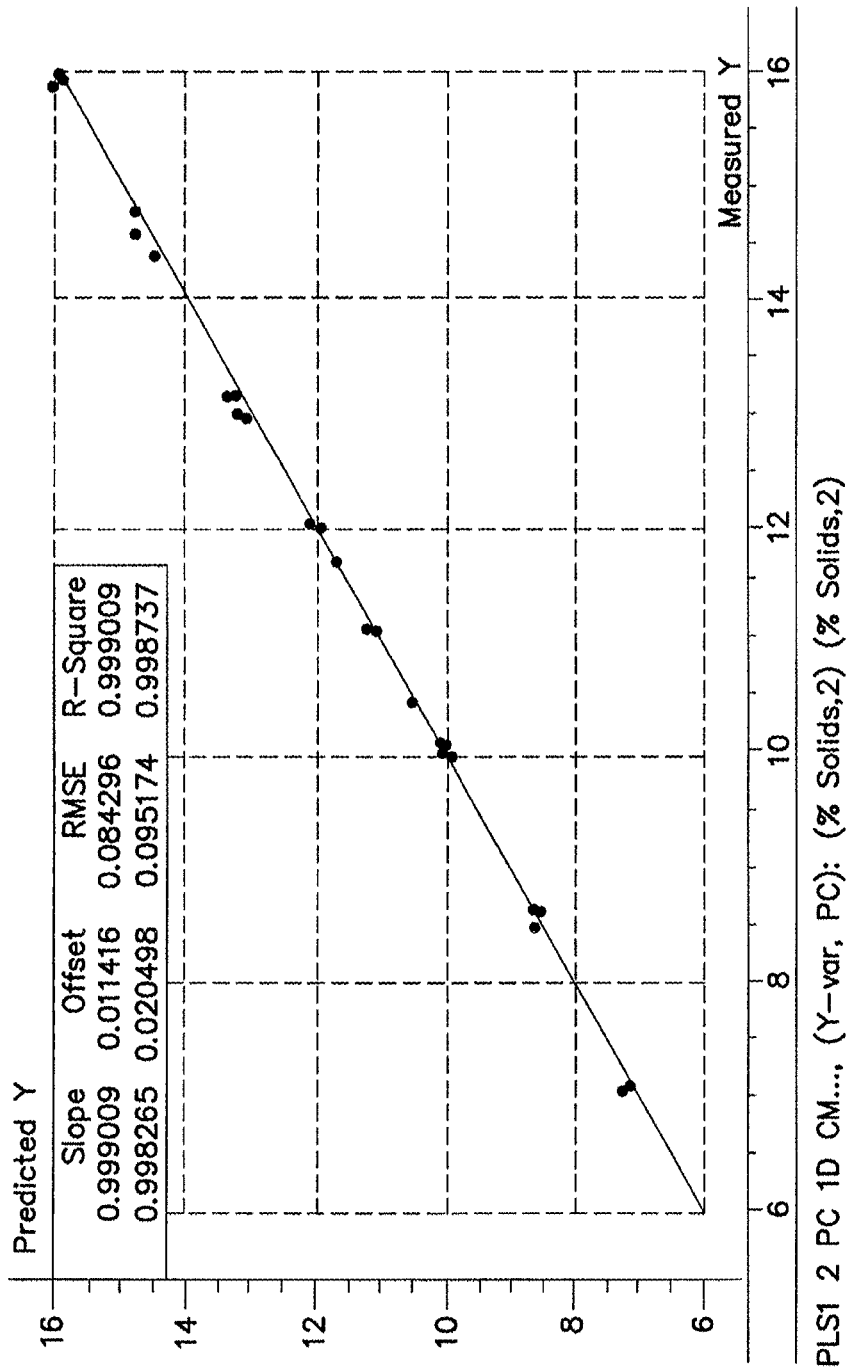
FIG. 6 is a graph that illustrates a calibration model, in accordance with embodiments of the invention.

The measured reference data (Y-data) is used to develop a calibration model for the chemometric software. The calibration model is designed such that processing of the Raman spectral data (X-data) produces a predicted value of weight percent of solids that matches the measured reference data (Y-data). A plot of the calibration model with the optimum number of PCs is shown in FIG. 6. The measured Y values are plotted on the horizontal axis, and the predicted Y values are plotted on the vertical axis.

Certain parameters are given after a PLS calibration has been performed, which can be utilized to evaluate the quality of the model. If improvement in quality is desired, omitting spectral data from certain wavenumber regions of the PLS calibration and mathematical pretreatment are often utilized. The model is evaluated with spectra of samples not utilized in the model development, referred to as validation.

Figure 7:
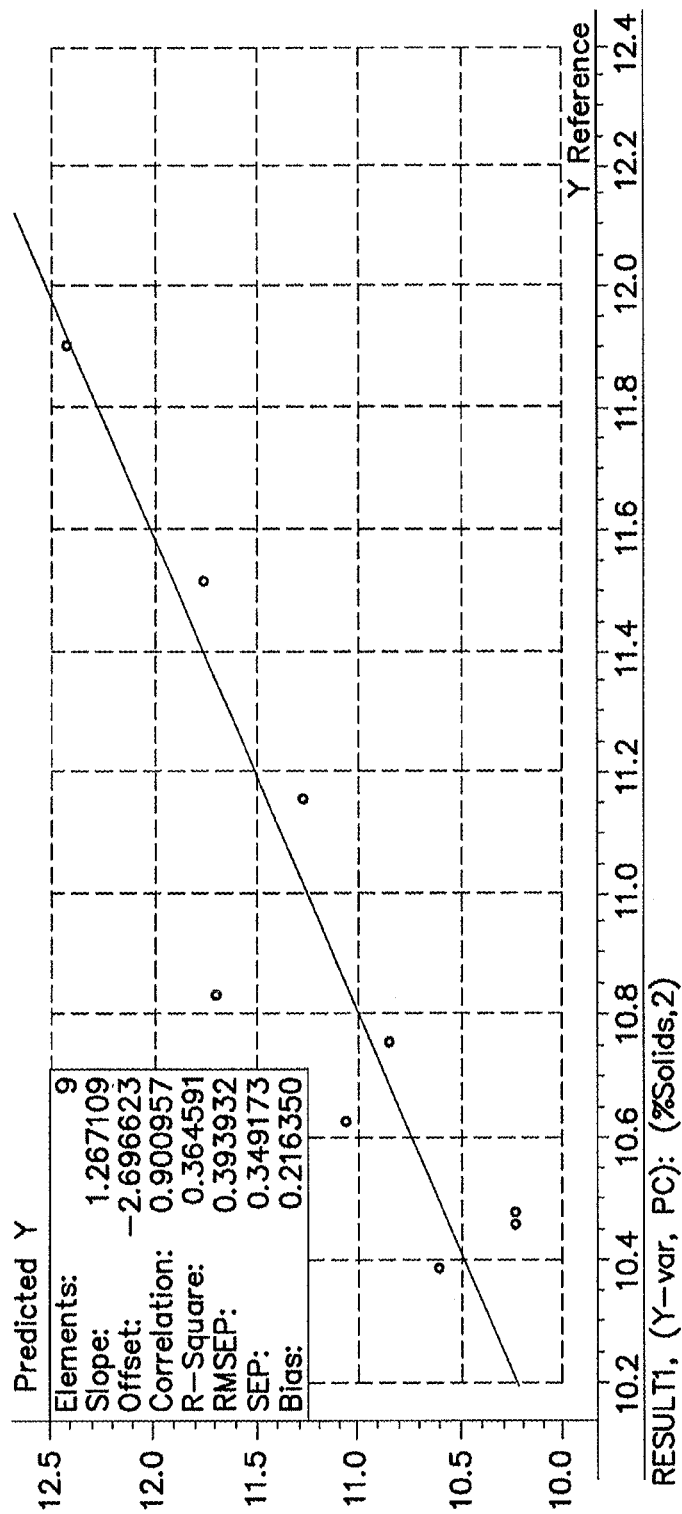
FIG. 7 is a graph that illustrates model validation, in accordance with embodiments of the invention.

A plot of model validation results is shown in FIG. 7. The measured reference data is plotted on the horizontal axis, and the predicted value is plotted on the vertical axis. Performance over a range of 10% solids to 12% solids was evaluated. The data in FIG. 6 demonstrates that accuracy, as estimated from RMSE, may be greater than 90%. Depending on the type of information needed for a particular suspension, lower accuracies may be acceptable, which depend on application requirements.

EXAMPLE 1

This experiment was performed to measure and determine the percent solid in a suspension consisting of Technosphere (FDKP) particles in water (aqueous suspension). A Raman spectrometer model RXN3 (Kaiser Optical Systems, Inc.) was used. The Raman Spectrometer was set using the parameters as described in FIG. 4. The Technosphere suspension was placed in a 20 ml beaker and stirred during the Raman spectral sampling. Spectral sampling consisted of 8 sample accumulations of 45 seconds each. Four of the eight accumulations were performed for cosmic ray filtration. The Raman spectra acquired were transferred to the Unscrambler (chemometric software) and analyzed according to the model as shown in FIG. 3, Step 214. The Raman spectral data obtained was used to generate a partial least square calibration model with corresponding sample data on percent solid obtained using a reference microwave loss on drying technique.

The percent accuracy was determined by dividing the root mean square error (RMSE) generated by the output over the mean percent solid value obtained for all samples and subtracting from 100. The formula for RMSE is given as:

$$RMSE(P) = \sqrt{\frac{\sum_{i=1}^{n}(y_a - y_p)^2}{n}}$$

where $y_a$ is the measured (reference) value, $y_p$ is the predicted value, and n is the number of observations.

A resultant calibration model is shown in FIG. 6. Table 1 shows the calibration model reference data of predicted and measured values obtained.

TABLE 1

| Sample No. | Measured (Reference) Value | Predicted Value |
|---|---|---|
| 1 | 7.10 | 7.12 |
| 2 | 8.64 | 8.53 |
| 3 | 10.10 | 9.99 |
| 4 | 11.11 | 11.03 |
| 5 | 12.01 | 11.89 |
| 6 | 13.19 | 13.17 |
| 7 | 14.64 | 14.74 |
| 8 | 15.96 | 15.93 |
| 9 | 7.08 | 7.18 |
| 10 | 8.66 | 8.62 |
| 11 | 10.01 | 9.90 |
| 12 | 11.12 | 11.10 |
| 13 | 11.73 | 11.66 |
| 14 | 13.00 | 13.01 |
| 15 | 14.45 | 14.46 |
| 17 | 16.00 | 15.96 |
| 18 | 7.05 | 7.24 |
| 19 | 8.50 | 8.62 |
| 20 | 10.03 | 10.03 |
| 21 | 11.15 | 11.17 |
| 22 | 12.07 | 12.05 |
| 23 | 13.04 | 13.13 |
| 24 | 14.83 | 14.76 |
| 25 | 15.89 | 16.04 |
| 26 | 10.13 | 10.04 |
| 27 | 10.48 | 10.50 |
| 28 | 13.20 | 13.30 |
| Mean | 11.52 | 11.52 |

The data show that the percent accuracy for measuring solids in a suspension using the present techniques is 99.27% within the range of 7 to 16% solids.

Having thus described several aspects of several embodiments of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

The invention claimed is:

1. A method for determining weight percent of solids in a suspension, comprising:
   mixing the suspension;
   acquiring Raman spectral data of the solids in the suspension; and
   processing the Raman spectral data to determine weight percent of the solids in the suspension.

2. A method as defined in claim 1, wherein the weight percent of the solids in the suspension is in a range of 5% to 20%.

3. A method as defined in claim 1, wherein the solids are microparticles of a diketopiperazine.

4. A method as defined in claim 3, wherein the microparticles have a size in a range of 0.1 to 34 micrometers.

5. A method as defined in claim 3, wherein acquiring Raman spectral data includes acquiring data in a range of 1180 to 1800 cm$^{-1}$ and a range of 2782 to 3136 cm$^{-1}$.

6. A method as defined in claim 1, wherein processing the Raman spectral data includes executing a partial least squares algorithm with Savitzky-Golay first derivative data pretreatment.

7. A method as defined in claim 1, wherein processing the Raman spectral data includes executing a Partial Least Squares algorithm using two principal components.

8. A method as defined in claim 1, wherein the Raman spectral data is processed by a computing device executing a partial least squares algorithm with data pretreatment.

9. A method as defined in claim 1, wherein processing the Raman spectral data includes executing a regression algorithm comprising a partial least squares, multiple linear regression, or principal component regression, with or without data pretreatment.

10. A method as defined in claim 9, wherein the data pretreatment is selected from multiplicative and extended multiplicative scatter correction, standard normal variate, various derivatives, and normalizations.

11. Apparatus for determining weight percent of solids in a suspension, comprising:
    a Raman spectrometer to acquire Raman spectral data of the solids in the suspension; and
    a computing device including a processor and a computer-readable storage medium, the computer-readable storage medium containing computer instructions that, when executed by the processor, perform a method of processing the Raman spectral data to determine weight percent of the solids in the suspension.

12. Apparatus as defined in claim 11, wherein the Raman spectrometer includes a short focus optical device adapted for immersion in the suspension.

13. Apparatus as defined in claim 12, wherein the Raman spectrometer and the method of processing the Raman spectral data are configured to determine weight percent of microparticles of a diketopiperazine.

14. Apparatus as defined in claim 13, wherein the Raman spectrometer is configured to acquire Raman spectral data in a range of 1180 to 1800 cm$^{-1}$ and a range of 2782 to 3136 cm$^{-1}$.

15. Apparatus as defined in claim 11, wherein the Raman spectrometer is configured to acquire Raman spectral data in less than 10 minutes.

16. Apparatus as defined in claim 11, wherein the Raman spectrometer is configured to acquire Raman spectral data for an exposure time of 45 seconds and for 4 accumulations, and to perform cosmic ray filtration.

17. Apparatus as defined in claim 11, wherein the processing of the Raman spectral data includes executing a Partial Least Squares algorithm with Savitzky-Golay first derivative data pretreatment.

18. Apparatus as defined in claim 11, wherein the Raman spectral data is processed by the computing device executing a Partial Least Squares algorithm with data pretreatment.

19. Apparatus as defined in claim 11, wherein processing the Raman spectral data includes executing a regression algorithm comprising a partial least squares, multiple linear regression, or principal component regression, with or without data pretreatment.

20. Apparatus as defined in claim 19, wherein the data pretreatment is selected from multiplicative and extended multiplicative scatter correction, standard normal variate, various derivatives, and normalizations.

* * * * *